(12) United States Patent
Armistead

(10) Patent No.: US 9,962,517 B2
(45) Date of Patent: May 8, 2018

(54) TEE-BEAM-RETAINED, ERGONOMICALLY PRE-CONTOURED, VALVED URINARY CATHETER WITH EXTERNAL ACTUATION TENSOR FOR CONTINUAL IN-PLACE COMPENSATION FOR BENIGN PROSTATE HYPERPLASIA

(71) Applicant: John Anderson Armistead, Easley, SC (US)

(72) Inventor: John Anderson Armistead, Easley, SC (US)

(*) Notice: Subject to any disclaimer, the term of this patent is extended or adjusted under 35 U.S.C. 154(b) by 342 days.

(21) Appl. No.: 14/998,671

(22) Filed: Feb. 1, 2016

(65) Prior Publication Data
US 2017/0216559 A1   Aug. 3, 2017

(51) Int. Cl.
*A61M 25/00* (2006.01)
*A61M 25/04* (2006.01)
*A61M 27/00* (2006.01)
*A61M 39/22* (2006.01)

(52) U.S. Cl.
CPC ........ *A61M 25/0017* (2013.01); *A61M 25/04* (2013.01); *A61M 27/00* (2013.01); *A61M 39/22* (2013.01)

(58) Field of Classification Search
CPC .. A61M 25/0017; A61M 25/04; A61M 27/00; A61M 39/22
See application file for complete search history.

(56) References Cited

U.S. PATENT DOCUMENTS

2011/0245810 A1* 10/2011 Armistead ........ A61M 25/0017
604/544

* cited by examiner

*Primary Examiner* — Benjamin Klein

(57) ABSTRACT

Problems associated with BPH can be negated using the present ergonomically pre-contoured, valved urinary catheter. To insert, the flexible tee beam is oriented on axis with the upper catheter. It will self-toggle into the tee orientation once inside the bladder, because of a small-bore elastic tubing that extends full length inside the main catheter. The catheter assembly will remain in place until the user tugs down hard enough on the outside-the-body, small diameter, valve-actuation tensor to cause the tee beam to fold double and be small enough to be pulled from the urethra. Lesser tugs actuate the compact, distal-end valve to allow urine flow. The smooth outer surfaces of the catheter assembly will help assure that reproductive functions will not be affected.

4 Claims, 2 Drawing Sheets

TEE-BEAM-RETAINED, ERGONOMICALLY PRE-CONTOURED, VALVED URINARY CATHETER WITH EXTERNAL ACTUATION TENSOR FOR CONTINUAL IN-PLACE COMPENSATION FOR BENIGN PROSTATE HYPERPLASIA

BACKGROUND OF THE INVENTION

Prostate enlargement, with the resulting restriction of urine flow, is a health issue that will affect a large majority of men as they age. Drugs; herbal therapy; stints; thermal or microwave tissue reduction; laser tissue removal; or surgical tissue removal are possible corrections for an enlarged prostate. So to is lifelong dependency on intermittent catheter use, for those not agreeable to, or suited for, the above treatments.

The present invention has as an objective being a more convenient, less costly and less dangerous correction of the symptoms of prostate enlargement compared to some of the treatments presently being used. And such will correct the symptoms of benign prostate hyperplasia without severely interfering with a man's reproductive capacity, nor his sexual performance.

The present application, as well as the apt earlier patent application by this inventor, has a user-actuated valve that will allow urine to flow on demand. That is in contrast to having continuous-drip urine flow into a bag, as with a Foley catheter. The latter is retained inside the bladder via a fluid-inflated bulb. The improvements inherent in the present invention relate mainly to the means of retaining the valved catheter inside the bladder; the way in which the catheter is inserted and removed; and having the flow valve be very compact so as to reduce bruising of the adjacent body tissues.

For the purpose of this patent application, it should be assumed that the suggested product construction materials will conform to, or surpass, the standards of health and safety recommended for products that remain in contact with body tissue. It should be noted, however, that this invention isn't a surgical implant, but is a product that can be inserted and removed by the user, without expected difficulty nor complications.

BRIEF SUMMARY OF THE INVENTION

An enlarged prostate reduces the cross-section of the upper urethra. Any catheter that can pass through the prostate will allow a rate of urine flow that is proportional to the internal cross-section of the catheter, or to the cross-section of the opening(s) between that catheter and the bladder. The larger sizes will drain urine more quickly. But those also tend to be more difficult to insert, and more prone to bruise or abrade the urethra, or to irritate the meatus at the tip of the penis.

Catheters made of a rubber-like material have thicker walls than plastic catheters with the same internal cross-sectional area. Catheters need to be sufficiently stiff to allow such to be pushed through the urethra without buckling. The portion of the urethra just below the prostate has a fairly pronounced bend. That is where the most resistance is encountered to having a catheter be inserted. It is also a part of the urethra most easily bruised by a large and/or stiff catheter—such as while sitting, or in changing position.

The present invention will optimize the urine flow rate through the catheter tubing, while having a small enough overall diameter, and/or being flexible enough in consistency, so as not to physically injure the curved lower urethra; the curved prostate urethra portion; nor the bladder neck area.

The involuntary musculature of the bladder sphincter can dilate and expel objects the size of a typical glass marble. But inserting objects that size up through the curved prostate urethra—and tubular objects in particular—would normally be a medical process that requires anesthesia. Such fact negates using a fixed-size, enlarged-end retention device for a valved catheter. The present invention uses aflexible tee beam that is stitched at its center to a small and very elastic tubing that extends down the full length of the inside of the catheter. The distal end of such is attached to a compact valve assembly. During insertion, the tee beam is oriented nearly parallel to the axis of the upper part of the main catheter tubing, with one hemispherical end of such bearing against a metal stiffener insert that is inside the proximal end of the catheter. The nested tee beam can reorient its alignment axis, much like a ball joint, to match the curvature of the portion of the urethra through which it is being pushed, and it is small enough in cross section to easily be pushed through the prostate urethra and into the bladder.

During the catheter insertion process, the urethra walls give lateral support to the axially-aligned tee beam, allowing such to remain nested inside the metal stiffener at the top of the main catheter tubing. When the tee beam enters the bladder, there are no bodily structures on all sides capable of maintaining nominal axial alignment with the upper urethra, allowing the tension in the small elastic tubing, that is stitched at the center of the tee beam with monofilament line, to cause the tee beam to toggle nearly perpendicular to the upper axis of the main catheter tubing.

During the assembly of the device, the latter monofilament line is inserted through a short section of low friction, thin-wall PEEK tubing that is positioned between the upper catheter wall and a catheter-end-stiffening section of stainless steel tubing. That location keeps the tee beam outside the lumen of the upper catheter opening, while restricting side-to-side motion of the tee beam, to assure that the projecting arms of such overlap the bladder neck sufficiently to prevent the involuntary expulsion of the device from the bladder. The flexible tee beam is sufficiently stiff to retain the device in the bladder, but is not so stiff as to prevent the tee beam from bending double when the distal end of the main catheter tubing, or the small elastic tubing therein, is deliberately tugged downward. A spherical silver bead is bonded to a separate section of the same type small elastic tubing to serve as a tensor to allow the user to actuate the adjacent, compact valve assembly, or by pulling down more firmly, to remove the device from the body.

There are two modes of usage of the present invention that differ only in the relative lengths of the main catheter tubing and the beaded-end, small tensor tubing that extends from the end of the penis. In mode one, the distal end of the main catheter extends outside the flaccid penis, so that the urine will go from the bladder into the toilet fixture without it contacting the urethra. When the user has an erection, the short, would-be-exposed portion of the lower catheter will be engulfed into the urethra. That will allow having a normal sex life. Very importantly: The sperm and the seminal fluid will pass easily over the outside of the smooth catheter tubing. Since there has been no surgical cutting away of the upper prostate portions, there should be no retrograde ejaculations into the bladder. Once the penis returns to its flaccid state, the lower end of the catheter will again be exposed to view. That process will be facilitated by the normal, expulsive muscular contractions of the urethra.

In usage mode two—probably the primary one for this device—the main catheter tubing is shortened so as to place the small, compact catheter valve well inside the urethra. That allows the distal end of the urethra to serve as the conduit for urine once such exits the valve. The comfort advantage for the man is not having a palpable catheter tubing inside the lower urethra. Instead, there is only a 1/16" diameter elastic tubing. When urination occurs, it exits the meatus. In both modes of usage, something as simple as a large paperclip can grip the beaded end of the tensor tubing for actuating the compact catheter valve without getting urine on the user's hands. The most simple means of placement utilizes an eight inch length of a more torsion resistant, straight section of tubing pushed over the catheter valve and retained by friction, until the tee beam engages inside the bladder. Once that happens, the insertion tubing, that contains the silver bead and tensor tubing that were initially threaded therein, can be pulled off the valve, leaving just the silver bead and two or three inches of the tensor tubing extending from the penis.

Unlike a Foley catheter, that can have the inflated bulb become incrusted with particulate matter from the urine, the present invention has very little surface area that is in continuous contact with the urine. Even so, it would be advisable to remove the present valved catheter every four to six weeks. To do that, the user simply pulls downward on the silver bead slightly more strongly than for actuating the valve. That increases the bending stress in the flexible tee beam tubing, causing such to double up. Because the removal direction is downward, the tubing of the folded up tee beam will be restrained, laterally, by the walls of the urethra until the entire valved catheter assembly has been removed. The whole process should take no more than a minute. While the catheter is out, normal urination can be experimented with.

User comfort is enhanced, because the main catheter tubing is ergonomically pre-curved to match the serpentine shape of a typical man's urethra. That pre-curved shape greatly reduces bending stresses that could bruise the urethra, while still being flexible enough to be inserted and to adapt to the changing urethra geometry. Note: The latter consideration of user comfort has been lacking in much of the prior art of other inventors.

DETAILED DESCRIPTION OF THE INVENTION

Note: The following description explains the construction of the present catheter invention, and the relationship of its various parts. However, the following does not discuss the medical and physiological considerations of the design which have already been clearly explained in the Brief Summary of the Invention. Please refer to the latter in order to understand the objective functionality of the present catheter invention as a medical device.

A primary consideration for devices inserted into the human body is having the components be compact enough not to cause discomfort during insertion or during utility. The male urethra, 3, is a variable serpentine shape, partially determined by the changing position, size and physiology of the enlarged prostate, 1. In general, there will be greater comfort when the flexible, main catheter tubing, 17, is ergonomically pre-contoured. That shape is produced by inserting each precision-cut-to-length blank of the chosen plastic tubing type into a serpentine groove machined into an aluminum mold, that is then heated to a precise temperature; for a precise amount of time; followed by a gradual cool-down before removing the still flexible but now pre-curved tubing components from the mold.

Figure 1:
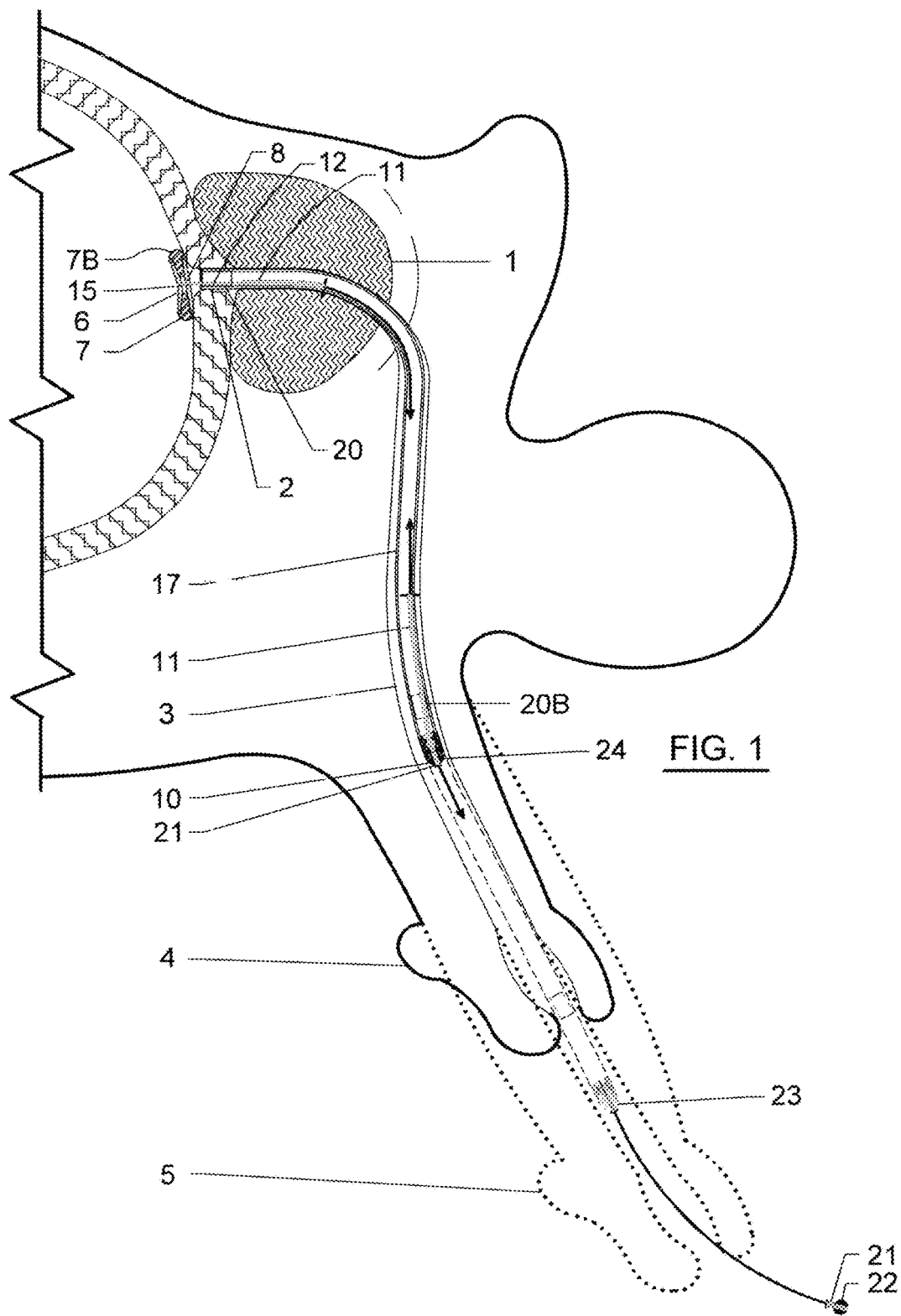
FIG. 1 indicates a schematic sectional view of the entire catheter assembly relative to the anatomy of the user. The flexible tee beam that is inside of the bladder is shown in longitudinal, midline section, though in actuality, such tee beam can rotate 360 degrees as determined by the bladder shape at the time.
Figure 2:
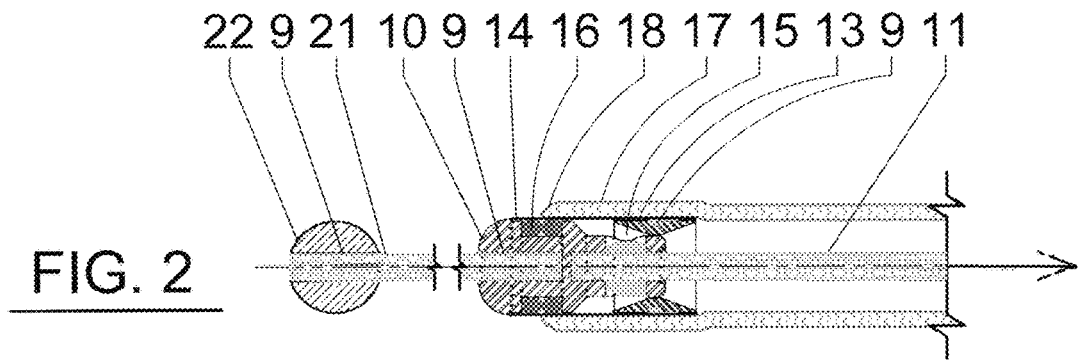
FIG. 2 shows an enlarged sectional view of the distal end of the closed catheter valve.

The present urinary catheter valve assembly is located on the distal end of the flexible, main catheter tubing, 17, that can be in either of two locations: mode one valve location, 23, is outside of the flaccid penis, 4; while the mode two valve location, 24, is entirely inside the urethra, 3, near the start of the first urethra curve as shown in FIG. 1. As seen in FIG. 2, the valve consists of a stainless steel valve core, 10, that has a recess for two side-by-side silicone O-rings, 16, that in the valve-closed position seat against a short stainless steel valve housing tube, 14. The latter, that is bonded into the distal end of the flexible, main catheter tubing, 17, with fluid type cyanoacrylate adhesive, has a rounded end, 18. The proximal end of the stainless steel valve core, 10, is bonded with gel type cyanoacrylate adhesive, 9, that has been injected into transverse hole, 15, to retain the distal end of a small-bore elastic tubing, 11. The latter normally has about an ounce of pretension to keep the stainless steel valve core, 10, in the closed position until a user actuates the valve by pulling outward on the small-bore tubing tensor, 21, that has a small silver bead, 22, bonded to its distal end with gel type cyanoacrylate adhesive, 9.

Figure 3:
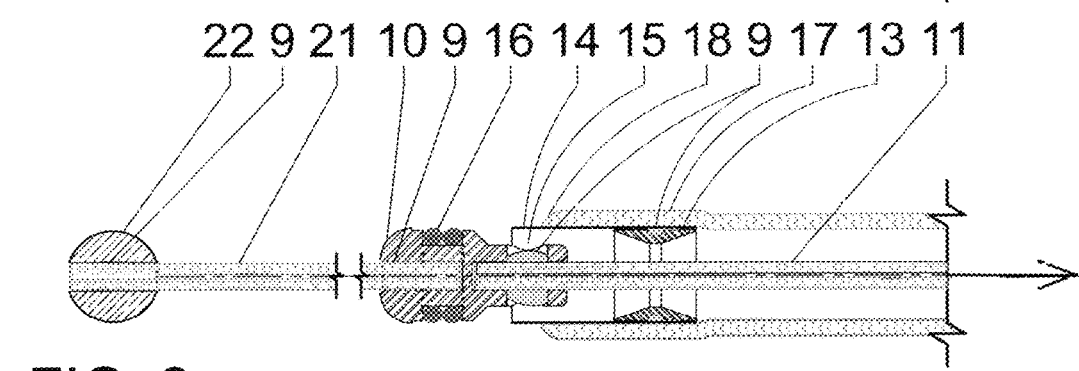
FIG. 3 shows a similar enlarged sectional view of the distal end of the open catheter valve.

To keep the stainless steel valve core, 10, axially aligned with the stainless steel valve housing tube, 14, when the small-bore elastic tubing, 11, is pulling at an angle, a stainless steel valve-core-alignment bushing, 13, having both ends with a slight internal bevel, is bonded to the proximal end of the stainless steel valve housing tube, 14, to mate with the proximal end of stainless steel valve core, 10, when such valve is in the closed position. As shown in FIG. 3, when the user pulls outward on silver bead, 22, the valve core is moved outward as well, so that the silicon O-rings, 16, no longer seat against the inside of the stainless steel valve housing tube, 14, allowing urine that is inside of the flexible main catheter tubing, 17, to flow around the small-bore elastic tubing, 11, through the stainless steel bushing, 13, and between the proximal end of the stainless steel valve core, 10, and the distal end of the stainless steel valve housing tube, 14. In mode one, urine can flow directly into the toilet fixture. In mode two, the distal end of a man's urethra will serve as the final conduit of the urine into the toilet fixture.

As shown in FIG. 1, a short section of stainless steel tubing, 20B, is friction retained, or bonded, inside of the flexible main catheter tubing, 17, to allow the user to restrain the in-and-out motion of the latter during the valve closing and valve opening processes. The two-fold objective is to keep the user's fingers far enough away from the valves 23 and 24 so that the fingers won't interfere with the valve function; and to limit the in-and-out axial movement of the flexible main catheter tubing, 17, to reduce irritation of the urethra, 3, and the bladder neck, 2.

Figure 4:
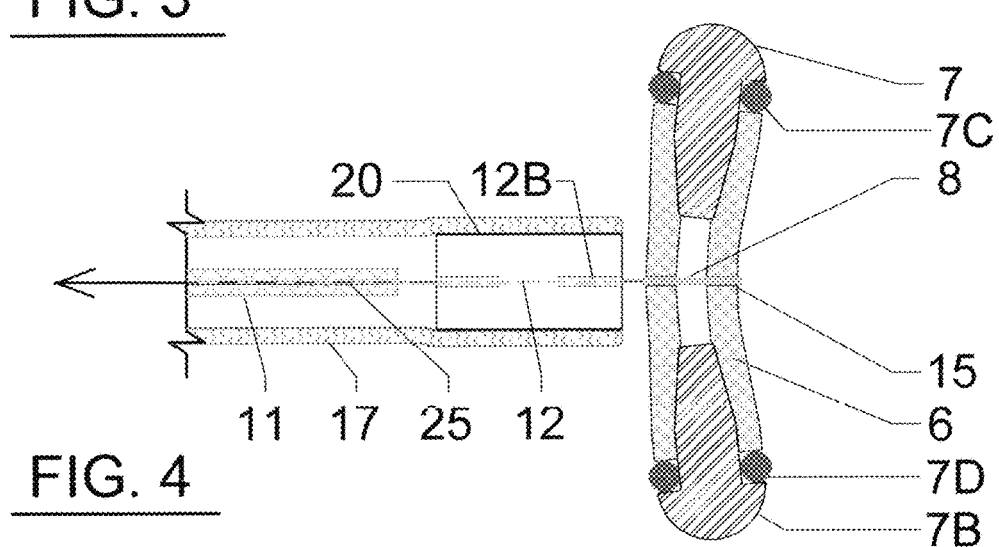
FIG. 4 shows the proximal end of the catheter assembly, with the tee beam schematically indicated as centering over the outer edge of the main catheter tubing, leaving 100% of its lumen unobstructed.

A tee beam assembly, as seen in FIG. 4, retains the catheter assembly inside the body. The former is composed of a highly flexible plastic tubing, 6, having a tube expanding, ball-ended stainless steel closure, 7, inserted into one end, and a same-shape stainless steel, tube-expanding insert, 7B, inserted into the opposite end. Between the would-be-abutting junctures of the above are edge-buffering silicone O-rings, 7C and 7D, that protect the bladder from possible irritation. The middle of the highly flexible plastic tubing, 6, has a laser drilled transverse hole, 15, large enough to allow attaching the tee beam assembly, using the monofilament tensile intermediary, 12. The latter is thrice-inserted, 8, in the proximal direction, to form a slip-resistant attachment without requiring knots nor an adhesive. The distal end of the monofilament tensile intermediary, 25, attaches without adhesives, into the small-bore elastic tubing, 11, and is held in place entirely by friction. The monofilament tensile intermediary, 12, passes through a thin-wall, low-friction section of PEEK tubing, 12B, that is located between the stainless steel stabilizing bushing, 20, and the proximal end of the main catheter tubing, 17, to keep the tee beam assembly to one side of the latter in order to improve urine flow and make the tee beam assembly more resistant to involuntary expulsion through the bladder neck, 2.

The tee beam assembly, as seen in FIG. 4, can be inserted into the bladder by first aligning such on axis with the proximal end of the flexible, main catheter tubing, 17, such that either ball-ended stainless steel tubing closure, 7 or 7B, will nest into the stainless steel stabilizing bushing, 20. In the process of so aligning the parts, the small-bore elastic tubing, 11, will be stretched far enough so that there will be several ounces of force holding the parts in compression. Once either ball-ended, stainless steel tubing closure, 7 or 7B, is inserted into the urethra, 3, the sides of such will maintain the nominal axial alignment of the tee beam assembly. But once the tee beam assembly has been pushed into the bladder, where there is no longer any side support, the monofilament tensile intermediary, 12, that is tugging downward, will cause the tee beam assembly to toggle approximately perpendicular to the flexible main catheter tubing, 17. In the latter position, the tee beam assembly has maximum bearing on the edges of the bladder neck, 2. When the user desires to remove the catheter assembly, he simply pulls down hard enough on the silver bead actuator, 22, until the flexible tee beam tube, 6, buckles double—much the way a garden hose can be buckled to shut off the flow. In the latter, folded-up orientation, the resistance of the bladder neck, 2, is overcome, and the tee beam can pass out of the penis.

The insertion of the shorter mode two catheter is facilitated by using a removable, more-torsion-resistant straight and square-cut tubing section, fitted over the stainless steel valve core, 10, and over the distal end of the short, stainless steel valve housing tube, 14. Friction will keep the coupling active until the tee beam assembly deploys, allowing the insertion tubing extension to simply be pulled out. Once a valved catheter has been installed, such can be left in place for up to six weeks—which is a preferable solution to benign prostate hyperplasia than the others described in Background of the Invention.

(End of Detailed Description of the Invention)

The invention claimed is:
1. A valved urinary catheter, comprising:
   a main catheter tube (17),
   a flexible tee beam tube (6),
   an O-ring sealed, stainless steel urine-flow valve (10),
   an elastic tubing (11) having a diameter smaller than the main catheter tube,
   a tubing tensor (21) having a silver bead tip,
   a monofilament line (25),
   wherein along its entire inside length, the main catheter tube (17) receives the elastic tubing,
   wherein the elastic tubing attaches on its proximal end to the monofilament line, and is friction-retained within the inside diameter of the elastic tubing,
   wherein a proximal end of the monofilament line (25) is thrice-inserted through a transverse hole in the center of the flexible tee beam tube,
   wherein the flexible tee beam tube (6) is configured to be folded in order to remove the catheter, and to remain inside of the bladder while resisting lesser tugs needed to actuate a movable core of the O-ring sealed, stainless steel urine-flow valve,
   wherein the movable core of the O-ring sealed, stainless steel urine-flow valve is bonded to a distal end of the elastic tubing with cyanoacrylate gel adhesive,
   wherein the distal end of the elastic tubing is bonded to the proximal end of the tubing tensor,
   wherein the tubing tensor is configured to extend from the penis of a user and is arranged such that pulling on the tubing tensor opens the urine flow valve,
   wherein the urine flow valve is normally held closed by a tension in the elastic tubing,
   wherein external surfaces of the main catheter tube are smooth to facilitate the flow of inseminating fluids.

2. The valved urinary catheter according to claim 1, wherein,
   the movable core comprises a movable stainless steel valve core with recesses for two side-by-side silicone O-rings that seal against a short section of stainless steel tubing that is bonded into an externally-rounded, distal end of the main catheter tubing, and
   wherein the movable core has a bonded-in-place bushing at a proximal end of a valve housing with opposed incline bevels and an inside diameter larger than the outside diameter of the proximal end of the movable valve core to which it mates when the valve is in the closed position, and
   wherein the movable core is configured to resist off-axis tugs of the elastic tubing without substantially reducing the urine flow potential of the valve when in the open position, because the opposed incline bevels of the bushing will facilitate efficient fluid flow.

3. A method of inserting into a patient the valved urinary catheter according to claim 1 comprising:
   pulling outward on the tee beam tube until one end of the tee beam tube is nesting inside a distal end of, and in approximately common axial alignment with the main catheter tubing, so as to allow inserting the catheter with a ball-ended stainless steel tubing closure on an end of the flexible tee beam
   guiding the device through the sphincter muscles and through an enlarged prostate into the bladder where the small bore elastic tubing will automatically toggle the tee beam to be in an orientation approximately perpendicular to the end of the main catheter tube.

4. The valved urinary catheter according to claim 1, wherein:
   the urine flow valve is configured to be located just outside of a flaccid-state penis and to be engulfed into the urethra when the user has an erection; or the urine flow valve is configured to be located near a first bend of a male urethra; and further comprising:
   a valve housing, and
   a straight length of torsion resistant tubing configured to serve as an insertion tool that grips over an exposed distal end of the valve core and the distal end of the valve housing, wherein the torsion resistant tubing is configured to be disengaged once the catheter is retained inside the bladder by pulling outward, leaving the silver-bead tipped, tubing tensor extending from the penis.

\* \* \* \* \*